United States Patent [19]

Zöl et al.

[11] Patent Number: 4,849,530
[45] Date of Patent: Jul. 18, 1989

[54] PROCESS FOR THE PREPARATION OF CRYSTALLINE SALTS OR ARYLOXY-PROPANOLAMINES

[75] Inventors: Gerhard Zöl; Gerhard Pfarrhofer, both of Linz, Austria

[73] Assignee: Rorer Pharmaceutical Corporation, Fort Washington, Pa.

[21] Appl. No.: 203,390

[22] Filed: Jun. 6, 1988

Related U.S. Application Data

[62] Division of Ser. No. 935,917, Nov. 28, 1986, Pat. No. 4,767,784.

[30] Foreign Application Priority Data

Dec. 13, 1985 [DE] Fed. Rep. of Germany ....... 3544172

[51] Int. Cl.$^4$ .................. C07C 127/19; C07C 101/00
[52] U.S. Cl. ..................... 549/491; 558/303; 558/308; 560/19; 560/20; 560/101; 562/471; 562/472; 562/486; 562/490; 562/492; 562/491; 564/51; 564/52; 564/164; 564/165; 564/336; 564/347
[58] Field of Search ............ 564/51, 52, 164, 165, 564/169, 336, 347; 260/501.17, 501.11, 501.18, 502; 558/303, 308; 549/491; 560/19, 20, 101; 562/471, 472, 486, 490, 493

[56] References Cited

U.S. PATENT DOCUMENTS

| | | | |
|---|---|---|---|
| 2,079,962 | 5/1937 | Miescher et al. | 560/101 |
| 3,317,553 | 5/1967 | Crowther et al. | 260/501.17 |
| 3,501,769 | 3/1970 | Crowther et al. | 260/501.17 |
| 3,723,476 | 3/1973 | Nakanishi et al. | 260/501.17 |
| 4,034,009 | 7/1977 | Zolss et al. | 564/54 |
| 4,038,313 | 7/1977 | Wilhelm | 564/51 |
| 4,081,447 | 3/1978 | Prasad et al. | 562/427 |
| 4,460,586 | 7/1984 | Berthold | 544/313 |
| 4,767,784 | 8/1988 | Zölss et al. | 514/554 |

FOREIGN PATENT DOCUMENTS

| | | | |
|---|---|---|---|
| 1061341 | 8/1979 | Canada | 564/51 |
| 1061342 | 8/1979 | Canada | 564/51 |
| 3309595 | 9/1984 | Fed. Rep. of Germany | 564/51 |
| 1383899 | 2/1975 | United Kingdom | 564/51 |
| 1396322 | 6/1975 | United Kingdom | 564/51 |

OTHER PUBLICATIONS

Crowther et al.; Beta-Andrenergic Blocking Agents; M.Med.Chem (1971), vol. 14, 511–513.
Nakanishi et al.; Studies on Cardiovascular Drugs; J. Med. Chem (19/2), vol. 15, 45–48.
Bartsch et al.; Arzneim-Forsch, 27(1) Nr. 5 (1977), 1022–1026 Chemical Abstracts; vol. 102 (1985), No. 72332 g.

Primary Examiner—Richard L. Raymond
Assistant Examiner—Raymond Covington

[57] ABSTRACT

The invention relates to novel crystalline salts of aryloxypropanolamines with diphenylacetic acid, a process for their preparation and the use of these salts for the preparation of chemically pure aryloxy-propanolamines or pharmaceutically acceptable salts thereof.

4 Claims, No Drawings

PROCESS FOR THE PREPARATION OF CRYSTALLINE SALTS OR ARYLOXY-PROPANOLAMINES

This is a division of application Ser. No. 935,917, filed on Nov. 28, 1986, now U.S. Pat. No. 4,767,784.

The invention relates to novel crystalline salts of aryloxy-propanolamines with diphenylacetic acid, a process for their preparation and the use of these salts for the preparation of chemically pure aryloxy-propanolamines or pharmaceutically acceptable salts thereof.

A number of variously substituted 1-aryloxy-3-amino-2-propanols and pharmaceutically acceptable salts thereof have interesting pharmacological properties and have already been included in the range of medicaments available. Compounds from this class of substance are available for various fields of indication, the beta-receptor blocking action, in particular, being in the foreground. Examples of highly effective compounds are N'-(3-acetyl-4-(3-((1,1-dimethylethyl)amino)-2-hydroxypropoxy)phenyl)-N,N-diethylurea (celiprolol), 1-(4-(2-methoxyethyl)phenoxy)-3-((1-methylethyl)amino)-2-propanol (metoprolol) or 1-((1-methylethyl)amino)-3-(1-naphthyloxy)-2-propanol (propranolol).

Various synthesis processes are available for the preparation of aryloxy-propanolamines, these processes being described by the example of celiprolol, inter alia, in U.S. Pat. No. 4,034,009, Canadian Patent Specification No. 1,061,342 or Canadian Patent Specification No. 1,061,341.

Very high requirements are imposed on the purity of the aryloxy-propanolamines in view of their medical use. In particular, the preparations which are used in human medicine should either contain no by-products at all from the synthesis, or only the slightest traces of these products. Crude products containing impurities, removal of which again and again meets with difficulties, are formed when the known synthesis processes are carried out industrially for the preparation of 1-aryloxy-3-amino-2-propanols, for example by reaction of a corresponding 1-aryloxy-2,3-epoxy-propane or a 1-aryloxy-3-("leaving group"-substituted)-2-propanol with an amine containing the desired substituent (in this context, compare A. F. Growther et al. J. Med. Chem. 1971, Volume 14, No. 6, pages 511–513). There is therefore still a need for novel purification processes for aryloxypropanolamines which are technically easy to carry out and, in particular, should enable, in particular, relatively large amounts of impurities and by-products formed in the synthesis to be removed without trace in a simple manner.

It has now been found, unexpectedly, that aryloxy-propanolamines form, with diphenylacetic acid, novel, readily crystallizing salts which enable the aryloxy-propanolamines to be separated out as crystals from solutions of the crude products obtained in the preparation and thereby guarantee excellent success for the purification. The aryloxy-propanolamines can be regenerated in a simple manner from these diphenylacetates with the degree of purity required for medical use, or converted into pharmaceutically acceptable salts.

The invention accordingly relates to salts of aryloxy-propanolamines with diphenylacetic acid, of the general formula

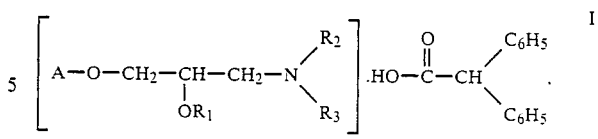

in which

A denotes (a) a substituted phenyl radical of the general formula

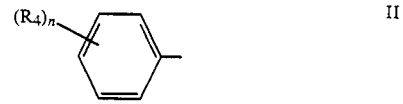

in which n represents an integer from 1 to 4, the substituents $R_4$ are either identical or different and independently of one another represent lower alkyl, C-2- or C-3-lower alkenyl, $C_5$ or $C_6$-cycloalkyl, lower alkoxy, C-2- or C-3-lower alkenoxy, cycloalkylalkoxy, tetrahydrofuranyl-methoxy, lower alkoxy-lower alkyl, lower alkanoyl, halogen, hydroxyl, cyano, carboxamido, acyloxy or radicals of the formula

in which X in the formulae III and IV in turn represents carbamoyl, alkylcarbamoyl, dialkylcarbamoyl, ureido, N'-alkylureido, N'-cycloalkylureido, N,N'-dialkylureido, N',N'-dialkylureido or alkoxycarbonylamino and m in the formula IV represents zero or an integer from 1 to 3, (b) a fused-on polynuclear aromatic or hydroaromatic radical which can be mono- or polysubstituted by hydroxyl and/or can contain one or more oxo groupings, or (c) an indoyl, methylindolyl, carbostyryl, carbazolyl or 4-morpholinyl-2,1,3-thiadiazolyl radical, $R_1$ denotes hydrogen or a straight-chain or branched $C_2$ to $C_2$-alkanoyl or aroyl radical, $R_2$ denotes hydrogen and $R_3$ denotes a branched $C_3$ to $C_6$-alkyl radical, a phenyl-lower alkyl or indoyl-lower alkyl radical which is straight-chain or branched and is unsubstituted or substituted by hydroxyl or alkoxy, or a radical of the formula

in which, in formula V, l represents the integer 1 or 2 and Y represents an N'-phenylureido, N'-pentamethyleneureido, N'-3''-oxapentamethyleneureido or unsubstituted or substituted phenylacetyl-amino radical, or $R_2$ and $R_3$, bonded to one another and together with the adjacent nitrogen atom, denote an unsubstituted or substituted 5-or 6-membered saturated heterocyclic radical.

If A in formula I represents a substituted phenyl radical of the general formula II, the substituent or substituents $R_4$ as lower alkyl denote, for example, ethyl, propyl, isopropyl, butyl, isobutyl, tert.-butyl or, in particular, methyl, as 2- or 3-lower alkenyl denote, for example, 2- or 3-butenyl, 1- or 2-methallyl or, preferably, allyl (2-propenyl), and as $C_5$- or $C_6$-cycloalkyl denote, for example, cyclopentyl or cyclohexyl. Lower alkoxy denotes, for example, ethoxy, propoxy, isopropoxy, butoxy, isobutoxy or, in particular, methoxy, 2- or 3- lower alkenoxy denotes, for example, 2- or 3-butenyloxy or, in particular, allyloxy (2-propenyloxy) and lower alkoxy-lower alkyl denotes, in particular, 2- or 3-lower alkoxy-lower alkyl, such as, for example, 2-ethoxy-, 2-propoxy-or 2-butoxy-ethyl, 2- or 3-methoxypropyl, 2- or 3-ethoxypropyl or, preferably, 2-methoxyethyl. $R_4$ as lower alkanoyl denotes, for example, propionyl, butyryl or, preferably, acetyl, and as halogen denotes fluorine, bromine, iodine or, in particular, chlorine.

The term carboxamido in $R_4$ represents the radical of an aliphatic carboxylic acid amide, which is formed by removing a hydrogen from the $NH_2$ group of the amide, preferably the acetamido, propionamido or butyramido radical. Acyloxy preferably denotes the acetoxy radical.

If $R_4$ represents radicals of the formulae III or IV, in these formulae the term carbamoyl or alkylcarbamoyl or dialkylcarbamoyl in X denotes the group

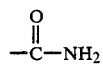

or such a group in which one or both hydrogen atoms of the $-NH_2-$ radical of this group are replaced by lower alkyl with the above meaning, for example methylcarbamoyl, ethylcarbamoyl, dimethylcarbamoyl, diethylcarbamoyl and the like. A ureido radical or substituted ureido radical X in the formulae III and IV represents the group

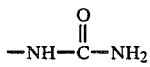

or such a group in which one or two hydrogens of this group are replaced, at the point designated by the notation on the nitrogen, by lower alkyl or cycloalkyl, in each case with the abovementioned meaning, for example N'-methylureido, N,N'-dimethylureido, N'-ethylureido, N'-isopropylureido, N'-cyclohexylureido, N',N'-dimethylureido or, in particular, N',N'-diethylureido.

X as alkoxycarbonylamino represents a lower alkylcarbamate radical

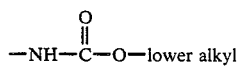

with the meaning given above for lower alkyl.

A as a fused-on aromatic or hydroaromatic radical which can be mono- or polysubstituted by hydroxyl and/or can contain one or more oxo groupings is, for example, the 1-naphthyl, 2-naphthyl, 6,7-dihydroxy-1-naphthyl, 5-hydroxy-1-naphthyl, 5,6,7,8-tetrahydro-6,7-dihydroxy-1-naphthyl, 5,6,7,8-tetrahydro-5-oxo-1-naphthyl, 9-fluorenon-4-yl or inden-4-yl radical.

A as indolyl is to be understood as a radical of 2,3-benzopyrrole, A as carbostyryl is to be understood as a radical of 2-hydroxy-quinoline, and A as carbazolyl is to be understood as a radical of dibenzopyrrole.

$R_1$ as a straight-chain or branched $C_2$ to $C_5$-alkanoyl radical denotes, for example, propionyl, butyryl, isobutyryl or, preferably, acetyl or 2,2-dimethylpropionyl (pivaloyl), and as an aroyl radical denotes, for example, substituted or unsubstituted benzoyl.

$R_3$ as a branched $C_3$ to $C_6$-alkyl radical preferably denotes isopropyl, tert.-butyl or tert.-pentyl, and as a straight-chain or branched phenyl-lower alkyl or indolyl-lower alkyl which is unsubstituted or substituted by hydroxyl or alkoxy preferably denotes the 2-phenethyl, 2-(3,4-dimethoxyphenyl)ethyl or 2-indolyl-1,1-dimethylethyl radical. Y as N'-phenylureido or N'-pentamethyleneureido or N'-3''-oxapentamethyleneureido in formula V represents a ureido radical in which a hydrogen on the terminal N atom is replaced by phenyl, or a ureido radical in which the terminal N atom, together with the methylene chain, forms a piperidino or morpholino radical, and as an unsubstituted or substituted phenylacetyl-amino radical in formula V represents a group of the formula

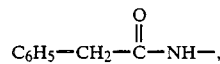

it being possible for one or more hydrogen atoms on the phenyl radical of this group to be replaced, for example by hydroxyl.

If $R_2$ and $R_3$ are bonded to one another and together with the adjacent nitrogen atom form an unsubstituted or substituted five- or six-membered saturated heterocyclic radical, this can contain no hetero atoms or a further hetero atom in addition to the nitrogen. Five-or six-membered saturated heterocyclic rings without a further hetero atom are, for example, pyrrolidino or piperidino. Five- or six-membered rings which contain an additional hetero atom include those rings in which the additional hetero group is NH, N-lower alkyl, N-phenyl, O or S, such as pyrazolidino, morpholino, thiomorpholino, piperazino or N-lower alkyl- or N-phenyl-piperazino, for example N-(2-methoxyphenyl)-piperazino.

Because of their excellent tendency towards crystallization and the particularly pronounced purification effect, the novel salts of the general formula I of the following aryloxy-propanolamines are particularly preferred: N'-(3-acetyl-4-(3-((1,1-dimethylethyl)amino-2-hydroxypropoxy)phenyl-N,N-diethylurea (celiprolol), 1-((1-methylethyl)amino)-3-(1-naphthyloxy)-2-propanol (propranolol), 1-(2,3-dimethylphenoxy)-3-((1,1-dimethylethyl)amino-2-propanol (xibenol), 1-(4-(2-methoxyphenyl)piperazin-1-yl)-3-((3,4,5-trimethoxy)phenoxy)-2-propanol (encipranzine), 1-(2,5-dichlorophenoxy)-3-((1,1-dimethylethyl)amino)-2-propanol (cloranolol), 1-(2-chloro-5-methylphenoxy)-3-((1,1-dimethylethyl)amino)-2-propanol (bupranolol) 1-(4-(2-methoxyethyl)phenoxy)-3-((1-methylethyl)amino)-2-propanol (metoprolol), 4-(2-hydroxy-3-((1-methylethyl)amino)propoxy)phenylacetamide (atenolol), N-(3-acetyl-4-(2-hydroxy-3-((1-methylethyl)amino)propoxy)phenyl)acetamide (diacetolol), 1-((1-methylethyl)amino)-3-(2-(2-propenyloxy)phenoxy)-2-propanol (oxprenolol), 1-((1,1-dimethylethyl)amino)-3-(2-((tetrahydro-2-furanyl)methoxy)phenoxy)-2-propanol (bufetolol), 1-(3-methylphenoxy)-3-((2-(3,4-dimethoxyphenyl)ethyl)amino)-2-propanol (bevantolol), 2-(3-((1,1-dimethylethyl)amino)-2-hydroxypropoxy)benzonitrile (bunitrolol), N-(3-acetyl-4-(2-hydroxy-3-((1-methylethyl)amino)propoxy)phenyl)butyramide (acebutolol), 1-((1,1-dimethylethyl)amino)-3-((4-(morpholinyl)-2,1,3-thiadiazol-5-yl)-2-propanol (timolol), N-(2-((3-(2-cyanophenoxy)-2-hydroxy-propyl)amino)ethyl)-2-(4-hydroxyphenyl)-acetamide (epanolol), 2-(2-hydroxy-3-((2-(1H)-indol-3-yl-1,1-dimethylethyl)amino)-propoxy-benzonitrile (bucindolol), 5-(3-(1,1-dimethylethyl)amino)-

2-hydroxy-propoxy)-3,4-dihydro-1-(2H)-naphthalinone (bunolol), 2-(3-((1,1-dimethylpropyl)amino)-2-hydroxy-propoxy)-benzonitrile (penirolol), 1-(2,4-dichloro-phenoxy)-3-(3,4-dimethoxy-beta-phenylethylamino)-2-propanol, 4-(2-hydroxy-3-((1-methyl-3-phenylpropyl)-amino)-propoxy)phenyl-acetamide and N-(2-((3-(2-cyanophenoxy-2-hydroxypropyl)amino)ethyl-N'-phenylurea.

The novel salts of the general formula I are prepared by reacting an aryloxy-propanolamine of the general formula

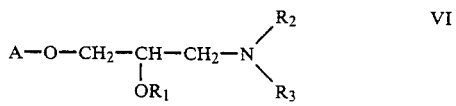

in which A, $R_1$, $R_2$ and $R_3$ have the meaning given under formula I, with at least the stoichiometric amount of diphenylacetic acid in a solvent or solvent mixture which is inert towards the reaction partners, at temperatures from room temperature up to the boiling point of the solvent or of the lowest-boiling solvent component, separating off the diphenylacetate of the formula I which deposits at room temperature or, preferably, at low temperatures from the reaction mixture obtained in this reaction and, if appropriate, recrystallizing it from an organic solvent.

The salts of the general formula I are obtained, for example, by direct reaction of solutions of an aryloxy-propanolamine of the formula VI and diphenylacetic acid in suitable solvents. Such solvents which may be mentioned are, inter alia, aliphatic alcohols, such as methanol, ethanol, propanol, isopropanol, butanol and the like; chlorinated hydrocarbons, such as methylene chloride, chloroform, carbon tetrachloride and the like; aliphatic carboxylic acid amides, carboxylic acid esters or carboxylic acid nitriles, such as dimethylformamide, dimethylacetamide, ethyl acetate, acetonitrile and the like, aliphatic ketones, such as acetone, methyl ethyl ketone and the like; mixtures containing these solvents or mixtures of these solvents with water. A particularly preferred solvent for the reaction according to the invention is acetone.

Virtually any desired reaction temperature can be chosen within the abovementioned limits, but the reaction is preferably carried out at room temperature or temperatures which are just above or below room temperature.

The salts of the formula I according to the invention are also obtained, however, by salt conversion, for example by reaction of corresponding salts of an aryloxy-propanolamine of the formula VI, such as hydrohalides, preferably the hydrochloride, or the sulfates, with suitable salts of diphenylacetic acid, for example alkali metal salts, preferably sodium or ammonium salts. For this, the starting materials are dissolved in suitable solvents and added to one another. An adequate solubility difference between the aryloxypropanolamine salt used as the starting material and the diphenylacetate of the formula I is essential, and the inorganic salt formed as a by-product, for example sodium chloride, should be easy to separate off. Examples of suitable solvents for the salt conversion are water, lower aliphatic alcohols, such as methanol or ethanol, or aliphatic ketones, such as acetone or methyl ethyl ketone, carboxylic acid amides, carboxylic acid nitriles, such as dimethylformamide, dimethylacetamide or acetonitrile, mixtures containing these solvents or mixtures of these solvents with water.

The diphenylacetates of the general formula I according to the invention have an exceptionally high tendency towards crystallization and also separate out of the aryloxy-propanolamine solutions, which contain impurities and/or by-products of organic or inorganic nature, in a pure form without including foreign substances or forming mixed crystals. They are therefore outstandingly suitable for crystalline deposition of the aryloxy-propanolamines with a high degree of purity from solutions of their crude products, whilst impurities and by-products remain in solution.

After being separated off from the reaction mixture, the diphenylacetates of the formula I are usually obtained in such a pure form that further purification steps, for example by recrystallization or reprecipitation, are no longer necessary. In the few cases in which the diphenylacetates are not obtained in the degree of purity necessary for their further use for the preparation of aryloxy-propanolamines or of pharmaceutically acceptable salts thereof for medicinal purposes they can be purified again in a simple manner by recrystallization from organic solvents. Examples of such suitable solvents are lower aliphatic alcohols, such as methanol, ethanol, propanol, isopropanol, butanol and the like, aliphatic ketones, such as acetone, methyl ethyl ketone and the like, carboxylic acid esters or carboxylic acid nitriles, such as ethyl acetate, acetonitrile and the like.

It is therefore not necessary for the aryloxy-propanolamines of the formula VI to be employed in a pure form for the preparation of the diphenylacetates of the general formula I.

A particular advantage of the salts according to the invention is that these are also obtained in a pure form if the crude product of an aryloxy-propanolamine such as is obtained in a synthesis process customary for these compounds, after removal from the reaction mixture and without a further purification step, is used for their preparation. A further advantage is that pure crystalline salts of the formula I are even obtained from oily crude products which cannot be crystallized and enable these to be purified in a high yield.

It is therefore possible for the preparation of the aryloxy-propanolamines and the subsequent conversion into the diphenylacetates of the general formula I also to be carried out in an advantageous manner in a one-pot reaction, by converting the basic aryloxy-propanolamines into the salts by addition of diphenylacetic acid immediately after their preparation.

The salts according to the invention are particularly suitable for the purification of crude products of aryloxy-propanolamines, such as are obtained by reaction of a 1-aryloxy-2,3-epoxypropane of the formula

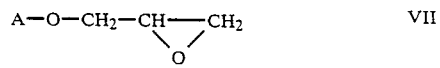

or a compound of the formula

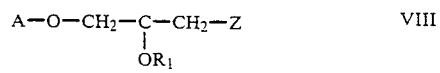

with an amine of the formula

in which, in the above formulae, A, $R_1$, $R_2$ and $R_3$ have the meaning given under formula I and Z represents a leaving group which can easily be split off. Such reactions are described, for example, in German Patent Specification No. 2,458,624, in German Offenlegungsschrift 3,039,848 or in J. Med. Chem. 1971, Volume 14, No. 6, pages 511–513.

The abovementioned reaction is a very simple, economic and frequently used process for the preparation of aryloxy-propanolamines. In particular, relatively large amounts of tertiary amines with two aryloxy-propanol radicals are formed as undesirable by-products in the preparation of 1-aryloxy-3-amino-2-propanols with a terminal secondary amino group, which are predominant in number because of their therapeutic importance and which can be obtained by the synthesis route mentioned by reaction of a compound of the formula VII or VIII with a primary amine of the formula IX. The purification of crude products from such a synthesis presents particular difficulties according to the prior art.

To simplify the purification, the formation of by-products in the form of the tertiary amines which proceeds as a competing reaction was hitherto suppressed by using a very large, for example up to 10-fold, excess of amine or completely bypassed by using amines which additionally carry a protective group which can easily be split off. Both methods have considerable disadvantages, however, and do not completely eliminate further purification operations, which are necessary to obtain the compounds with the degree of purity required for medicinal purposes. Thus, the amine employed in excess can usually be recovered only with corresponding losses, the dilution of the reaction mixture which necessarily arises in this method of working additionally effecting an adverse space/time yield. This method is completely unusable in those cases in which the excess amine has only a low volatility.

If protected amines are used, a further process step to remove the protective group must in turn be added to the synthesis of the aryloxy-propanolamines, which in any case usually comprises many stages, so that this method is also used only reluctantly in the preparation of the compounds on an industrial scale.

A surprising advantage of the salts according to the invention is thus that these can be separated off in a pure form from crude products which, in addition to tertiary amines and/or other impurities, contain, for example, only about 60% of the desired aryloxy-proanolamine, and permit purification of such crude products, which can be achieved only with great difficulty with the known purification processes. It is therefore possible for the synthesis process described above in more detail for aryloxy-propanolamines to be carried out in an economic and more advantageous manner with equivalent amounts or only small, for example two- to three-fold, excesses of the amine component, without purification of the crude products thereby obtained encountering difficulties which cannot be overcome.

Samples of salts of the general formula I which have been prepared from crude products of aryloxy-propanolamines of the formula VI have an exceptionally high degree of purity. Either no by-products and impurities at all or only the smallest amounts thereof have been found in such samples in investigations by chromatographic methods, such as thin layer chromatography or high pressure liquid chromatography, melting point investigations or spectroscopic methods, and these in no way impede further use of the salts of the formula I for the preparation of products for medicinal purposes.

The aryloxy-propoanolamines can be recovered from the diphenylacetates of the general formula I according to the invention in the customary manner, or can be converted into their pharmaceutically acceptable acid addition salts.

The present invention therefore also relates to the use of the pure salts of the general formula I obtained in one of the ways mentioned for the preparation of aryloxy-propanolamines of the general formula IV or of pharmaceutically acceptable salts thereof with the degree of purity necessary for medicinal use.

For this, the aryloxy-propanolamines of the general formula VI are recovered from the diphenylacetates of the general formula I in a manner which is known per se by addition of bases and, if desired, are then converted into pharmaceutically acceptable acid addition salts. This can be effected, for example, by dissolving the diphenylacetate in an organic water-immiscible solvent and then treating the resulting solution with a dilute aqueous solution of a base, such as sodium hydroxide solution, potassium hydroxide solution and the like. The organic phase can then be separated off, dried and evaporated in vacuo, the aryloxy-propanolamine remaining in a pure form. If desired, the basic compounds of the formula VI can then be converted into their acid addition salts with acids, such as are described, for example, in J. Pharm. Sci. 66, 1–16, for the preparation of therapeutically acceptable salts. Acids which are suitable for salt formation are, for example, strong mineral acids, such as hydrochloric, hydrobromic, hydriodic or hydrofluoric acid, sulfuric acid, phosphoric acid, nitric acid and perchloric acid, and aliphatic, alicyclic, aromatic or heterocyclic carboxylic acids or sulfonic acids, such as formic acid, acetic acid, propionic acid, succinic acid, fumaric acid, maleic acid, glycolic acid, lactic acid, malic acid, benzoic acid, salicylic acid, nicotinic acid, cyclohexylsulfonic acid, methanesulfonic acid or amidosulfonic acids and the like.

The diphenylacetates of the general formula I can be converted directly into pharmaceutically acceptable acid addition salts in a particularly advantageous and simple manner in a manner which is known per se, the diphenylacetate anion being replaced by a pharmaceutically usable anion. For salt conversion, the diphenylacetate is dissolved or suspended, for example, in an organic solvent and the solution or suspension is treated with an acid containing the desired anion, preferably with a strong mineral acid, such as hydrochloric, hydrobromic, hydriodic or hydrofluoric acid, sulfuric acid, phosphoric acid, nitric acid, perchloric acid and the like. It is essential for the salt conversion to obtain a sufficient solubility difference by choosing a suitable solvent in which the diphenylacetic acid liberated is readily soluble, whilst the aryloxy-propanolamine salt containing the anion of the desired acid should have only a poor solubility in this solvent and therefore precipitates.

Examples of suitable solvents are aliphatic ketones, such as acetone, methyl ethyl ketone and the like, aliphatic alcohols, such as propanol, isopropanol, butanol, isobutanol, tert.-butanol, amyl alcohol and the like, and carboxylic acid esters or carboxylic acid nitriles, such as ethyl acetate, butyl acetate, acetonitrile and the like.

Another advantage of the invention is that the diphenylacetic acid liberated can be recovered in a simple manner, usually in virtually quantitative yields, both in the recovery of the aryloxy-propanolamines from the diphenylacetates of the formula I by means of a base and in the salt conversion, and can be used again.

The following examples illustrate the invention in more detail, the yields of diphenylacetate of the formula I of course being different, depending on the degree of purity of the crude products employed.

EXAMPLES 1–6:

N'-(3-Acetyl-4-(3-((1,1-dimethylethyl)amino)-2-hydroxypropoxy)phenyl)-N,N-diethylurea (celiprolol) diphenylacetate A: 3-acetyl-4-(N',N'-diethylureido)phenyl
$R_1$: H
$R_2$: H
$R_3$: 1,1-dimethylethyl

EXAMPLE 1:

524.5 g of the crude product of N'-(3-acetyl-4-(3-((1,1-dimethylethyl)amino)-2-hydroxypropoxy)-phenyl)-N,N-diethylurea (water content 4.67%) obtained by one of the synthesis processes described below without a further purification step, corresponding to 500 g of the anhydrous crude product, are dissolved in 3,500 ml of acetone at 25° C., cloudiness present is removed and rinsed with 300 ml of acetone, the filtrate is cooled to 18° C. and a solution of 282 g of diphenylacetic acid (water content 0.82%) in 1,200 ml of acetone is added, whereupon the diphenylacetate of the base employed starts to crystallize out. To bring the crystallization to completion, the mixture is cooled with cold water for 4 hours and the crystals which have precipitated are filtered off with suction, rinsed with 1,500 ml of acetone and dried in air.

Yield: 740 g (94.9% of theory)
Melting point 140°–142° C.

The diphenylacetate thus obtained is analytically pure and exhibits a uniform spot in a thin layer chromatogram in the following mobile phases:

Mobile phase I: benzene/acetone/glacial acetic acid/water; 40/50/30/20; v/v/v/v
Mobile phase II: ethyl acetate/ethanol/2N NH$_4$OH; 50/25/20; v/v/v
Development: UV

EXAMPLE 2:

10.0 g of a crude product of N'-(3-acetyl-4-(3-((1,1-dimethylethyl)amino)-2-hydroxypropoxy)phenyl)-N,N-diethylurea hydrate are dissolved in 150 ml of acetonitrile and a solution of 5.6 g of diphenylacetic acid in 50 ml of acetonitrile is added.

The crystals which have precipitated are filtered off with suction, after the mixture has stood at room temperature for 5 hours.

Yield: 14.3 g (96.1% of theory)
The diphenylacetate obtained is analytically pure.
Melting point: 140°–142° C.

EXAMPLE 3:

10.0 g of a crude product of N'-(3-acetyl-4-(3-((1,1-dimethylethyl)amino)-2-hydroxypropoxy)phenyl)-N,N-diethylurea hydrate are dissolved in 40 ml of ethanol, a solution of 5.6 g of diphenylacetic acid in 40 ml of ethanol is added, the reaction mixture is cooled at 0° C. overnight and the crystals which have precipitated are filtered off with suction.

Yield: 7.1 g (47.7% of theory)
The resulting diphenylacetate is analytically pure.
Melting point: 140°–142° C.

EXAMPLE 4:

2.0 g of a crude product of N'-(3-acetyl-4-(3-((1,1-dimethylethyl)amino)-2-hydroxypropoxy)phenyl)-N,N-diethylurea hydrate are dissolved in 50 ml of ethyl acetate, 1.12 g of diphenylacetic acid are added and the crystals which have precipitated are filtered off with suction, after one hour at room temperature.

Yield: 2.87 g (96.4% of theory)
The resulting diphenylacetate is analytically pure.
Melting point: 140°–142° C.

EXAMPLE 5:

2.0 g of a crude product of N'-(3acetyl-4-(3-((1,1-dimethylethyl)amino)-2-hydroxypropoxy)-phenyl)-N,N-diethylurea hydrate are dissolved in 5.0 ml of methanol, 1.12 g of diphenylacetic acid are added, 5 ml of water are added to the clear solution and the crystals which have precipitated are filtered off with suction, after 2 hours at room temperature.

Yield: 2.4 g (80.6% of theory)
The resulting diphenylacetate is analytically pure.
Melting point: 140°–142° C.

EXAMPLE 6:

2.0 g of a crude product of N'-(3-acetyl-4-((1,1-dimethylethyl)amino)-2-hydroxypropoxy)-phenyl)-N,N-diethylurea hydrate are dissolved in 20 ml of n-butanol, 1.12 g of diphenylacetic acid are added and the resulting crystals are filtered off with suction, after the mixture has stood overnight at room temperature.

Yield: 2.5 g (83.9% of theory)
The resulting diphenylacetate is analytically pure.
Melting point: 140°–142° C.

Preparation of the crude product used as the starting material:

Variant A:

365.4 g of tert.-butylamine (4.99 mol) are mixed with 261.8 ml of H$_2$O and the mixture is cooled to room temperature. 750 g of N'-(3-acetyl-4-(2,3-epoxypropoxy)phenyl)-N,N-diethylurea (2.45 mol) are then added and the mixture is reacted at a temperature of 24° to 27° C. for 8 hours.

750 ml of acetone are then added to the reaction mixture, the components are mixed, a total of 1,500 ml of water are slowly added at a maximum temperature of 25° C., the mixture is seeded and left to stand overnight at 3° C. and the base which has precipitated is centrifuged off. The crude product is suspended in a mixture of 200 ml of acetone and 1,800 ml of water, centrifuged and dried in air.

Yield of crude N'-(3-acetyl-4-(3-((1,1-dimethylethyl)amino)-2-hydroxypropoxy)phenyl)-N,N-diethylurea hydrate: 902.2 g (92.7% of theory)

This product is not a single compound in the thin layer chromatogram and, in addition to the main spot, exhibits several spots of larger or smaller Rf value which are to be attributed to impurities.

Variant B:

A mixture of 0.825 ml of tert.-butylamine (0.0078 mol) and 0.42 ml of water is added to 1.0 g of N'(3-acetyl-4-(3-bromo-2-hydroxy-propoxy)phenyl)-N,N-diethylurea (0.0026 mol) and the mixture is stirred at room temperature for 30 hours. The reaction mixture is concentrated in vacuo, water is added to the residue and the mixture is extracted with chloroform. After drying with $Na_2SO_4$, the chloroform solution is distilled in vacuo. The crude product of N'-(3-acetyl-4-(3-((1,1-dimethylethyl)amino)-2-hydroxy-propoxy)phenyl)-N,N-diethylurea which remains as the dry residue is used without further purification for the preparation of the diphenylacetate according to Examples 1-6.

Variant C:

1.0 g of N'-(3-acetyl-4-(3-chloro-2-hydroxypropoxy)-phenyl)-N,N-diethylurea (0.0029 mol) is reacted with a mixture of 0.924 ml of tert.-butylamine (0.0087 mol) and 0.46 ml of water at room temperature for 13 days. Working up is carried out as in variant B and the dry residue thereby obtained is used as the crude product for the preparation of the diphenylacetate according to Examples 1-6.

Variant D:

2.0 g (0.0042 mol) of N'-(3-acetyl-4-(3-tosyloxy-2-hydroxy-propoxy)-phenyl)-N,N-diethylurea are reacted with a mixture of 1.0 ml of tert.-butylamine (0.0095 mol) and 1.0 ml of water at room temperature for 18 hours. The reaction mixture is taken up in chloroform and washed twice with water and the organic phase is dried with $Na_2SO_4$ and distilled. The dry residue thereby obtained is used as the crude product for the preparation of the diphenylacetate according to Examples 1-6.

EXAMPLE 7:

1-((1-Methylethyl)amino)-3-(1-naphthyloxy)-2-propanol (propranolol) diphenylacetate A: 1-naphthyl
$R_1$: H
$R_2$: H
$R_3$: 1-methylethyl 6.44 g of a crude product of 1-((1-methylethyl)amino)-3-(1-naphthyloxy)-2-propanol are dissolved in 25 ml of acetone at 45° C., 5.27 g of diphenylacetic acid, which has first been dissolved in 10 ml of acetone under the influence of heat, are added and the reaction mixture is cooled. After the mixture has been left to stand in the cold, the crystals which have precipitated are filtered off with suction, washed with acetone and dried.

Yield: 9.3 g (78.97% of theory, based on the 1-(1-naphthoxy)-2,3-epoxy-propane) used for the preparation of the starting material).

The diphenylacetate exhibits a uniform spot in the thin layer chromatogram.

Melting point: 146°-148.5° C.

Preparation of the crude product used as the starting material:

2.55 ml of (1-methylethyl)amine (0.0297 mol) are mixed with 1.25 ml of $H_2O$ and the mixture is then stirred with 5 g of 1-(1-naphthyloxy)-2,3-epoxypropane (0.0249 mol) and reacted at room temperature for 23 hours.

The reaction product is taken up in $CHCl_3$, the mixture is extracted by shaking with water, the organic phase is separated off and the solvent is removed in vacuo.

6.44 g of a crude product of 1-((1-methylethyl)amino)-3-(1-naphthyloxy)-2-propanol, from which the pure substance can be separated off as crystalline diphenylacetate, are thus obtained as the dry residue.

EXAMPLE 8:

1-(4-(2-Methoxyphenyl)-piperazin-1-yl)-3-((3,4,5-trimethoxy)phenoxy)-2-propanol (enciprazine) diphenylacetate A: 3,4,5-trimethoxyphenyl
$R_1$: hydrogen
$R_2$ and $R_3$ together with the adjacent N atom: 4-(2-methoxyphenyl)-piperazin-1-yl 7.3 g of a crude product of 1-(4-(2-methoxyphenyl-piperazin-1-yl)-3-((3,4,5-trimethoxy)phenoxy)-2-propanol are dissolved in 35 ml of acetone, a solution of 3.6 g of diphenylacetic acid in 10 ml of acetone is added and the crystals which have precipitated are separated off, after the mixture has stood at 0° C. for 5 hours.

Yield: 8.5 g (77.19% of theory)

Melting point: 119°-120.5° C.

The diphenylacetate exhibits a uniform spot in the thin layer chromatogram in several systems.

Stationary phase: silica gel $HF_{60}$

Mobile phase I: benzene/methanol/acetone; 50/5/25; v/v/v

Mobile phase II: benzene/methanol; 25/50; v/v

Development: UV

Preparation of the crude product used as the starting material:

4.7 g of 1-(3,4,5-trimethoxy)phenoxy-2,3-epoxypropane (0.0196 mol) are reacted with 3.95 g of 1-(2-methoxy)-phenylpiperazine (0.0223 mol) in a mixture of 1.9 ml of water and 1.9 ml of ethanol at room temperature for 4 hours. The solvent is then stripped off in vacuo, diethyl ether is added to the residue and the product which has precipitated is filtered off with suction, after standing overnight.

7.4 g (90.61% of theory) of a crude product of 1-(4-(2-methoxyphenyl-piperazin-1-yl)-3-((3,4,5-trimethoxy)-phenoxy)-2-propoanol are thus obtained.

EXAMPLE 9:

1-(2,5-Dichlorophenoxy)-3-((1,1-dimethylethyl)amino)-2-propanol (cloranolol) diphenylacetate.

A: 2,5-dichlorophenyl
$R_1$: H
$R_2$: H
$R_3$: 1,1-dimethylethyl 8.55 g of a crude base of 1-(2,5-dichlorophenoxy)-3-((1,1-dimethylethyl)amino)-2-propanol in the form of an oily product are dissolved in 10 ml of acetone, a solution of 6.2 g of diphenylacetic acid in 25 ml of acetone is added and the crystals which have precipitated are filtered off with suction, after the mixture has stood at room temperature for 2 hours.

Yield: 12.4 g (86.8% of theory)

Melting point: 155°-156.5° C.

The diphenylacetate exhibits a uniform spot in the thin layer chromatogram in several systems.

Stationary phase: silica gel $HF_{60}$.

Mobile phase I: benzene/acetone/methanol/water; 40/50/30/20; v/v/v/v

Mobile phase II: benzene/methanol/$NH_4OH$; 50/12.5/0.1; v/v/v/v

Preparation of the crude product used as the starting material:

6.2 g of 1-(2,5-dichloro)-phenoxy-2,3-epoxypropane (0.0283 mol) are reacted in a mixture of 6 ml of (1,1-dimethylethyl)amine (0.057 mol) and 3 ml of water at room temperature for 24 hours.

The reaction mixture is concentrated in vacuo, the residue is taken up in methylene chloride, the organic phase is washed with water and dried with $Na_2SO_4$ and the solvent is distilled off.

8.55 g of a crude product of 1-(2,5-dichlorophenoxy)-3-((1,1-dimethylethyl)amino)-2-propanol are thus obtained in the form of an oily residue.

EXAMPLE 10:

1-(2,3-Dimethylphenoxy)-3-((1,1-dimethylethyl)amino)-2-propanol (xibenolol) diphenylacetate:

A: 2,3-dimethylphenyl
$R_1$: H
$R_2$: H
$R_3$: 1,1-dimethylethyl 1.6 g of the crude base of 1-(2,3-dimethylphenoxy)-3-((1,1-dimethylethyl)amino)-2-propanol in the form of an oily product which cannot be crystallized are dissolved in 5 ml of acetone, and a solution of 1.35 g of diphenylacetic acid in 5 ml of acetone is added. The crystals which have precipitated are filtered off with suction after the mixture has stood at room temperature for 1 hour.

Yield: 2.5 g (84.7% of theory)
Melting point: 148°–150° C.

The diphenylacetate exhibits a uniform spot in the thin layer chromatogram in several systems. Stationary phase and mobile phases as in Example 9

Development: spraying of the thin layer chromatography plate with 1% strength $I_2$ solution in ethanol.

Preparation of the crude product used as the starting material:

1.2 g of 1-(2,3-dimethyl)-phenoxy-2,3-epoxypropane are reacted with a mixture of 1.4 ml of (1,1-dimethylethyl)amine (0.013 mol) and 0.7 ml of water. The reaction mixture is concentrated in vacuo, the residue is taken up in methylene chloride and washed with water and, after drying, the organic phase is distilled.

1.69 g of a crude product of 1-(2,3-dimethylphenoxy)-3-((1,1-dimethylethyl)amino)-2-propanol are thus obtained in the form of an oily residue.

EXAMPLE 11:

1-(2-Cyano)-phenoxy-3-((1,1-dimethylpropyl)amino)-2-propanol (penirolol) diphenylacetate A: 2-cyanophenyl
$R_1$: H
$R_2$: H
$R_3$: 1,1-dimethylpropyl 1.87 g of the crude base of 1-(2-cyano)-phenoxy-3-((1,1-dimethylpropyl)amino)-2-propanol in the form of an oily product which cannot be crystallized are dissolved in 5 ml of acetone, a solution of 1.5 g of diphenylacetic acid in 3 ml of acetone is added and the crystals which have precipitated are separated off after the mixture has stood at room temperature for 1.5 hours.

Yield: 2.6 g (76.8% of theory, based on the 1-(2-cyano)-phenoxy-2,3-epoxy-propane employed for the preparation of the starting material.

A check on the purity in the thin layer chromatogram shows a uniform spot in several systems.

Stationary phase: silica gel $HF_{60}$
Mobile phase: benzene/acetone/glacial acetic acid/water; 50/30/20; v/v/v/v
Development: spraying with 1% strength iodine solution in ethanol Preparation of the crude product used as the starting material:

1.25 g of 1-(2-cyano)-phenoxy-2,3-epoxypropane (0.0071 mol) are reacted with a mixture of 1.24 g of (1,1-dimethylpropyl)amine (0.014 ml) and 0.8 ml of water at room temperature for 22 hours. The reaction mixture is concentrated in vacuo, the residue is taken up in chloroform, the mixture is washed with water, the organic phase is dried and the solvent is distilled off in vacuo.

1.87 g of a crude product of 1-(2-cyano)-phenoxy-3-((1,1-dimethylpropyl)amino)-2-propanol are thus obtained in the form of an oily residue.

The following novel salts of the general formula I were prepared from the crude products of the particular aryloxy-propanolamines and tested for their degree of purity, analogously to the working instructions given in Examples 1–11:

EXAMPLE 12:

N-(3-Acetyl-4-(2-hydroxy-3-((1-methylethyl)amino)-propoxy)phenyl)butyramide (acebutolol) diphenylacetate A: 2-acetyl-4-butyramido-phenyl
$R_1$: H
$R_2$: H
$R_3$: 1-methylethyl
Melting point: 108°–110° C.
Yield: 97.2% of theory

EXAMPLE 13:

1-((1-Methylethyl)amino)-3-(2-(2-propenyl)phenoxy)-2-propanol (alprenolol) diphenylacetate A: 2-(2-Propenyl)phenyl
$R_1$: H
$R_2$: H
$R_3$: 1-Methylethyl
Melting point: 91°–94° C.
Yield: 75.67% of theory

EXAMPLE 14:

4-(2-Hydroxy-3-((1-methylethyl)amino)propoxy)-phenylacetamide (atenolol) diphenylacetate A: 4-Carbamoylmethyl-phenyl
$R_1$: H
$R_2$: H
$R_3$: 1-Methylethyl
Melting point: 72°–74.5° C.
Yield: 97.5% of theory

EXAMPLE 15:

1-(3-Methylphenoxy)-3-((2-(3,4-dimethoxyphenyl)ethyl)amino-2-propanol (bevantolol) diphenylacetate A: 3-Methylphenyl
$R_1$: H
$R_2$: H
$R_3$: 2-(3,4-Dimethoxyphenyl)ethyl
Melting point: 146°–148° C.
Yield: 40.61% of theory

EXAMPLE 16:

2-(2-Hydroxy-3-((2-(1H)-indol-3-yl-1,1-dimethylethyl)amino)propoxy) benzonitrile (bucindolol) diphenylacetate A: 2-Cyanophenyl
$R_1$: H
$R_2$: H
$R_3$: -2-((1H)-indol-3-yl)-1,1-dimethylethyl
Melting point: 138°–140° C.
Yield: 56.96% of theory

EXAMPLE 17:

1-((1,1-Dimethylethyl)amino)-3-(2-((tetrahydro-2-furanyl)methoxy)phenoxy)-2-propanol (bufetolol) diphenylacetate A: 2-((Tetrahydro-2-furanyl)-methoxy)phenyl
$R_1$: H
$R_2$: H
$R_3$: 1,1-Dimethylethyl
Melting point: 125°–127° C.
Yield: 66.26% of theory

EXAMPLE 18:

2-(3-((1,1-Dimethylethyl)amino)-2-hydroxypropoxy)-benzonitrile (bunitrolol) diphenylacetate A: 2-Cyanophenyl
$R_1$: H
$R_2$: H
$R_3$: 1,1-Dimethylethyl
Melting point: 150°–152° C.
Yield: 75.94% of theory

EXAMPLE 19:

5-(3-((1,1-Dimethylethyl)amino)-2-hydroxypropoxy)-3,4-dihydro-1-(2H)-naphthalinone (bunolol) diphenylacetate A: 5,6,7,8-Tetrahydro-5-oxo-1-naphthyl
$R_1$: H
$R_2$: H
$R_3$: 1,1-Dimethylethyl
Melting point: 170°–172° C.
Yield: 75.25% of theory

EXAMPLE 20:

1-(2-Chloro-5-methylphenoxy)-3-((1,1-dimethylethyl)amino)-2-propanol (bupranolol) diphenylacetate A: 2-Chloro-5-methylphenyl
$R_1$: H
$R_2$: H
$R_3$: 1,1-Dimethylethyl
Melting point: 147°–149° C.
Yield: 60.84% of theory

EXAMPLE 21:

1-(9H-Carbazol-4-yloxy)-3-((1-methylethyl)amino)-2-propanol (carazolol) diphenylacetate:

A: 9H-Carbazol-4-yl
$R_1$: H
$R_2$: H
$R_3$: 1-Methylethyl
Melting point: 148°–150° C.
Yield: 62.5% of theory

EXAMPLE 22:

1-(2-Hydroxyquinolin-5-yloxy)-3-((1-methylethyl)amino)-2-propanol (carteolol) diphenylacetate A: 2-Hydroxyquinolin-5-yl
$R_1$: H
$R_2$: H
$R_3$: 1-Methylethyl
Melting point: 193°–195° C.
Yield: 63.16% of theory

EXAMPLE 23:

2-(2-(3-((1,1-Dimethylethyl)amino)-2-hydroxypropoxy)phenoxy)-N-methylacetamide (cetamolol) diphenylacetate A: 2-((Methylcarbamoyl)-methoxy)phenyl
$R_1$: H
$R_2$: H
$R_3$: 1,1-Dimethylethyl
Melting point: 146°–149° C.
Yield: 92.55% of theory

EXAMPLE 24:

N-(3-Acetyl-4-(2-hydroxy-3-((1-methylethyl)amino)-propoxy)phenyl)acetamide (diacetolol) diphenylacetate A: 2-Acetyl-4-acetamido-phenyl
$R_1$: H
$R_2$: H
$R_3$: 1-Methylethyl
Melting point: 143°–145.5° C.
Yield: 84.74% of theory

EXAMPLE 25:

N-(2-((3-(2-Cyanophenoxy)-2-hydroxy-propyl)amino)ethyl)-2-(4hydroxyphenyl)acetamide (epanolol) diphenylacetate A: 2-Cyanophenyl
$R_1$: H
$R_2$: H
$R_3$: 2-((4-Hydroxyphenyl)acetylamino)ethyl
Melting point: 170°–172° C.
Yield: 58.8% of theory

EXAMPLE 26:

1-((1H-Inden-4-yl)oxy)-3-((1-methylethyl)amino)-2-propanol (indenolol) diphenylacetate A: (1H)-Inden-4-yl
$R_1$: H
$R_2$: H
$R_3$: 1- Methylethyl
Melting point: 129°–130° C.
Yield: 86.02% of theory

EXAMPLE 27:

4-(2-Hydroxy-3-((1-methylethyl)amino-propoxy)-2,3,6-trimethylphenol-1-acetate (metipranol) diphenylacetate A: 4-Acetoxy-2,3,6-trimethylphenyl
$R_1$: H
$R_2$: H
$R_3$: 1-Methylethyl
Melting point: 109°–112° C.
Yield: 59.7% of theory

EXAMPLE 28:

1-((1-Methylethyl)amino-3-((2-methyl-1H-indol-4-yl)oxy)-2-propanol (mepindolol) diphenylacetate A: 2-Methyl-1-H-indol-4-yl
$R_1$: H
$R_2$: H
$R_3$: 1-Methylethyl
Melting point: 162°–165° C.
Yield: 91.5% of theory

EXAMPLE 29:

1-(2-Methoxyphenoxy)-3-((1-methylethyl)amino)-2-propanol (moprololol) diphenylacetate A: 2-Methoxyphenyl
$R_1$: H
$R_2$: H
$R_3$: 1-Methylethyl
Melting point: 118°–119° C.
Yield: 74.1% of theory

EXAMPLE 30:

1-(4-(2-Methoxyethyl)phenoxy)-3-((1-methylethyl)amino)-2-propanol (metoprolol) diphenylacetate A: 4-(2-Methoxyethyl)phenyl
$R_1$: H
$R_2$: H
$R_3$: 1-Methylethyl
Melting point: 99°–100° C.
Yield: 95.3% of theory

EXAMPLE 31:

5-(3-((1,1-Dimethylethyl)amino)-2-hydroxypropoxy)-1,2,3,4-tetrahydro-2,3-naphthalinediol (nadolol) diphenylacetate A: 5,6,7,8-Tetrahydro-6,7-dihydroxy-1-naphthyl
$R_1$: H
$R_2$: H
$R_3$: 1,1-Dimethylethyl
Melting point: 145°–148° C.
Yield: 69.3% of theory

EXAMPLE 32:

1-((1-Methylethyl)amino-3-(2-propenyloxy)phenoxy)-2-propanol (oxprenolol) diphenylacetate A: 2-(2-Propenyloxy)phenyl
$R_1$: H
$R_2$: H
$R_3$: 1-Methylethyl
Melting point: 96°–97.5° C.
Yield: 94.4% of theory

EXAMPLE 33:

N-(1-Methylethyl)-N'-(2-(4-(3-((1-methylethyl)amino)-2-hydroxypropoxy)phenyl)ethyl)urea (pafenolol) diphenylacetate A: 4-(2-(N'-(1-Methylethyl)-ureido)ethyl)-phenyl
$R_1$: H
$R_2$: H
$R_3$: 1-Methylethyl
Melting point: 85°–89° C.
Yield: 97.0% of theory

EXAMPLE 34:

N-(2-(4-(3-((1-Methylethyl)amino)-2-hydroxy-propoxy)phenyl)ethyl)methyl carbamate (pamatolol) diphenylacetate A: 4-(2-((Methoxycarbonyl)amino)ethyl)phenyl
$R_1$: H
$R_2$: H
$R_3$: 1-Methylethyl
Melting point: 94°–96° C.
Yield: 49.5% of theory

EXAMPLE 35:

1-(2-Cyclopentylphenoxy)-3-((1,1-dimethylethyl)amino)-2-propanol (penbutolol) diphenylacetate A: 2-Cyclopentylphenyl
$R_1$: H
$R_2$: H
$R_3$: 1,1-Dimethylethyl
Melting point: 103°–105° C.
Yield: 68.6% of theory

EXAMPLE 36:

1-(1H-Indol-4-yloxy)-3-((1-methylethyl)amino)-2-propanol (pindolol) diphenylacetate A: 1H-Indol-4-yl
$R_1$: H
$R_2$: H
$R_3$: 1-Methylethyl
Melting point: 128°–131° C.
Yield: 54.35% of theory

EXAMPLE 37:

N-(4-(2-Hydroxy-3-((1-methylethyl)amino)propoxy)-phenyl)acetamide (practolol) diphenylacetate A: 4-Acetamido-phenyl
$R_1$: H
$R_2$: H
$R_3$: 1-Methylethyl
Melting point: 86°–91° C.
Yield: 93.5% of theory

EXAMPLE 38:

N-Cyclohexyl-N'-(4-(3-((1,1-dimethylethyl)amino)-2-hydroxypropoxy)phenyl)urea (talinolol) diphenylacetate A: 4-(N'-Cyclohexylureido)phenyl
$R_1$: H
$R_2$: H
$R_3$: 1,1-Dimethylethyl
Melting point: 174°–177° C.
Yield: 89.2% of theory

EXAMPLE 39:

1-((1,1-Dimethylethyl)amino)-3-((4-morpholinyl-2,1,3-thiadiazol-5-yl)oxy)-2-propanol (timolol) diphenylacetate A: 4-Morpholinyl-2,1,3-thiadiazol-5-yl
$R_1$: H
$R_2$: H
$R_3$: 1,1-Dimethylethyl
Melting point: 131°–132° C.
Yield: 87.5% of theory

EXAMPLE 40:

1-(3-Methylphenoxy)-3-((1-methylethyl)amino)-2-propanol (toliprolol) diphenylacetate A: 3-Methylphenyl
$R_1$: H
$R_2$: H
$R_3$: 1-Methylethyl
Melting point: 90°–92° C.
Yield: 68.96% of theory

EXAMPLE 41:

N-(2-((3-(4-Hydroxyphenoxy)-2-hydroxy-propyl)amino)ethyl)-N'-3"-oxapentamethyleneurea (xamoterol) diphenylacetate A: 4-Hydroxyphenyl
$R_1$: H
$R_2$: H
$R_3$: 2-(N'-(3"-Oxapentamethylene)ureido)ethyl
Melting point: 140°–142° C.
Yield: 86.2% of theory

EXAMPLE 42:

1-(2,4-Dichlorophenoxy)-3-((2-(3,4-dimethoxy-phenyl)ethyl)amino)-2-propanol diphenylacetate A: 2,4-Dichlorophenyl
$R_1$: H
$R_2$: H
$R_3$: 2-(3,4-Dimethoxyphenyl)ethyl
Melting point: 130°–132° C.
Yield: 91.13% of theory

EXAMPLE 43:

4-(2-Hydroxy-3-((1-methyl-3-phenylpropyl)amino)-propoxy)phenylacetamide diphenylacetate A: 4-Carbamoylmethyl-phenyl
$R_1$: H
$R_2$: H
$R_3$: 1-Methyl-3-phenylpropyl
Melting point: 137°–140° C.
Yield: 83.85% of theory

EXAMPLE 44:

4-(3-((1,1-Dimethylethyl)amino)-2-pivaloyloxy-propoxy-9-fluorenone diphenylacetate A: 9-Fluorenon-4-yl
$R_1$: Pivaloyl
$R_2$: H
$R_3$: 1,1-Dimethylethyl
Melting point: 127°–128.5° C.
Yield: 82.9% of theory

EXAMPLE 45:

N-(2-((3-(2-Cyanophenoxy)-2-hydroxy-propyl)amino)ethyl)-N'-phenylurea diphenylacetate A: 2-Cyanophenyl
$R_1$: H
$R_2$: H
$R_3$: 2-(N'-Phenylureido)ethyl
Melting point: 140°–143° C.
Yield: 88.33% of theory

EXAMPLE 46:

1-((5-Hydroxy-naphth-1-yloxy)-3-((1-methylethyl)amino)-2-propanol

A: 5-Hydroxy-1-naphthyl
$R_1$: H
$R_2$: H
$R_3$: 1-Methylethyl
Melting point: 169°–174° C.
Yield: 86.46% of theory

EXAMPLE 47:

1-(4-((2-Cyclopropylmethoxy)ethyl)phenoxy)-3-((1-methylethyl)amino)-2-propanol (betaxolol)

A: 4-((2-Cyclopropylmethoxy)ethyl)phenyl
$R_1$: H
$R_2$: H
$R_3$: 1-Methylethyl
Melting point: 68°–70° C.
Yield: 78.8% of theory

EXAMPLE 48:

One-pot process 80 ml of dimethylsulfoxide and 170 ml of epibromohydrin are added to 100 g of N'-(3-acetyl-4-hydroxy)phenyl-N,N-diethylurea, 26.9 g of 91.5% strength potassium hydroxide solution are added under an argon atomosphere and the mixture is stirred at 30°–32° C. for 4 hours. When the reaction has ended, 120 ml of H₂O are added and the excess epibromohydrin is distilled off azeotropically in vacuo.

The residue is cooled, 83.7 ml of (1,1-dimethylethyl)amine (0.8 mol) and 83.7 ml of H₂O are added and the mixture is stirred overnight at 20° to 25° C. 50 ml of acetone and 20 ml of H₂O are added to the reaction mixture and the mixture is seeded. After crystallization has started, a further 230 ml of H₂O are added dropwise and the mixture is cooled to 5° C. for 5 hours. The crystals which have precipitated are filtered off with suction, washed with H₂O and dried in air. The residue of the crude base (145.4 g of N'-(3-acetyl-4-(3-((1,1-dimethylethyl)amino)-2-hydroxypropoxy)phenyl)-N,N-diethylurea hydrate) is dissolved in 850 ml of acetone at 27° C., the solution is clarified by filtration, a solution of 77.3 g of diphenylacetic acid in 250 ml of acetone is added and the diphenylacetate formed is made to crystallize initially without cooling and then at 0° C. for 4 hours. Yield of N'-3-acetyl-4-(3-((1,1-dimethylethyl)amino)-2-hydroxypropoxy)phenyl)-N,N-diethylurea (celiprolol) diphenylacetate: 192.65 g=89.4% of theory, based on the 145.4 g of N'-(3-acetyl-4-(3-((1,1-dimethylethyl)amino)-2-hydroxypropoxy)-phenyl)-N,N-diethylurea hydrate obtained as the crude base, see above, with a water content of 4.66% by weight.

Melting point: 140°–142° C.

The diphenylacetate thus obtained is analytically pure and exhibits a uniform spot in the thin layer chromatogram in several mobile phases.

EXAMPLE 49:

N'-(3-Acetyl-4-(3-((1,1-dimethylethyl)amino)-2-hydroxypropoxy)phenyl)-N,N-diethylurea (celiprolol)

5.9 g of the diphenylacetate obtained by one of Examples 1–6 are stirred in 50 ml of chloroform and 10 ml of 5% strength sodium hydroxide solution, the chloroform phase is separated off, dried over Na₂SO₄ and evaporated in vacuo and the crystalline residue is digested with a little acetone in the cold and filtered off with suction. 3.45 g of a product which is pure in the thin layer chromatogram are thus obtained in the form of colorless crystals of melting point 116°–118° C.

EXAMPLE 50:

N'-(3-Acetyl-4-(3-(1,1-dimethylethyl)amino)-2-hydroxypropoxy)phenyl-N,N-dimethylurea (celiprolol) hydrochloride.

625 g of a diphenylacetate obtained according to one of Examples 1–6 are suspended in 4,700 ml of acetone, 92.5 ml of water are added and the mixture is stirred at room temperature for 15 minutes.

92.5 ml of concentrated HCl (41.7 g of HCl in 100 ml) are then added, with stirring, and the mixture is left to stand first at room temperature for 30 minutes and then at +2° C. until crystallization is complete.

The resulting crystals are filtered off with suction, washed with acetone, suspended again in acetone, stirred for 1 hour, filtered off with suction again, rinsed and dried in air.

422.15 g (96.1% of theory) of hydrochloride which is pure in the thin layer chromatogram and has a melting point of 198°–200° C. are thus obtained.

Recovery of the diphenylacetic acid:

The acetone-containing mother liquor is concentrated to about 400 ml in vacuo, 1,200 ml of water are added, 20 ml of concentrated HCL are added and the diphenylacetic acid which has precipitated is filtered off with suction, washed with water and dried. The diphenylacetic acid recovered in this manner can be used again for the preparation of a diphenylacetate without further purification.

Yield: 219.0 g=97.7% of theory.

EXAMPLE 51:

1-((1-Methylethyl)amino)-3-(1-naphthyloxy)-2-propanol (propranolol) hydrochloride 9.3 g of a diphenylacetate obtained according to Example 7 are suspended in 93 ml of acetone, 2.48 ml of alcoholic HCl (29 g of HCl in 100 ml) are added and the hydrochloride which has separated out is filtered off with suction, after 1.5 hours, and washed with acetone.

Yield: 5.57 g (95.5% of theory)
Melting point: 163°–165° C.

The hydrochloride exhibits a uniform spot in the thin layer chromatogram in several systems.

Stationary phase: silica gel HF₆₀
Mobile phase: benzene/acetone/glacial acetic acid/water; 40/50/30/20; v/v/v/v
Development: UV or spraying with iodine solution the following aryloxy-propanolamines or pharmaceutically acceptable salts thereof were also prepared from the corresponding diphenylacetates by the working method described in Examples 47–49:

Enciprazine dihydrochloride: Melting point: 196°–197° C.
Cloranolol hydrochloride: Melting point: 210°–212° C.
Xibenolol: Melting point: 71°–72° C.
Acebutolol hydrochloride: Melting point: 141°–143° C.
Alprenolol hydrochloride: Melting point: 107°–109° C.
Atenolol: Melting point: 146°–148° C.
Bevantolol hydrochloride: Melting point: 137°–138° C.
Bucindolol hydrochloride: Melting point: 185°–187° C.
Bufetolol hydrochloride: Melting point: 153°–157° C.
Bunitrolol hydrochloride: Melting point: 163°–165° C.
Bunolol hydrochloride: Melting point: 225°–227° C.
Bupranolol hydrochloride: Melting point: 220°–222° C.
Carazolol hydrochloride: Melting point: 234°–235° C.
Carteolol hydrochloride: Melting point: 277°–278° C.
Cetamolol hydrochloride: Melting point: 145°–147° C.
Diacetolol: Melting point: 127°–130° C.
Indenolol hydrochloride: Melting point: 147°–148° C.
Metipranol: Melting point: 105°–107° C.
Mepindolol: Melting point: 100°–102° C.
Moprolol hydrochloride: Melting point: 110°–112° C.
Metoprolol hydrochloride: Melting point: 83° C.
Oxprenolol: Melting point: 78°–80° C.
Pafenolol
Pamatolol hydrochloride: Melting point: 106° C.
Penbutolol hydrochloride: Melting point: 123°–124° C.
Pindolol: Melting point: 171°–178° C.
Practolol: Melting point: 134°–136° C.
Talinolol: Melting point: 142°–144° C.
Timolol hydrochloride: Melting point: 161°–163° C.
Xamoterol hemifumarate: Melting point: 168°–169° C.
1-(2,4-Dichlorophenoxy)-3-((2-(3,4-dimethoxy-phenyl)-ethyl)amino)-2-propanol hydrochloride: Melting point=151°–152° C.
4-(2-Hydroxy-3-((1-methyl-3-phenylpropyl)amino)-propoxy)phenylacetamide: Melting point=106°–108° C.
4-(3-(1,1-Dimethylethyl)amino-2-pivaloyloxy-propoxy)-9-fluorenone hydrocloride: Melting point=228°–231° C.
N-(2-((3-(2-Cyanophenoxy)-2-hydroxy-propyl)-amino)-ethyl)-N'-phenylurea: Melting point=144°–145° C.
1-(4-(2-(Cyclopropylmethoxy)-ethyl)-phenoxy)-3-((1-methylethyl)-amino)-2-propanol hydrochloride: Melting point=116° C.

What we claim is:

1. A process for the preparation of a salt of an aryloxy-propanolamine with diphenylacetic acid of the formula

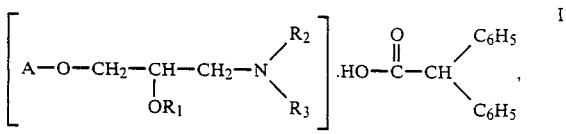

in which A is
(a) a substituted phenyl radical of the formula

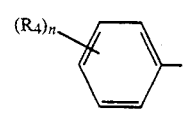

in which n represents an integer from 1 to 4, the substituents R₄ are either identical or different and independently of one another represent lower alkyl, C₂- or C₃- lower alkenyl, $C_5$- or $C_6$- cycloalkyl, lower alkoxy, $C_2$- or $C_3$- lower alkenoxy, cycloalkylalkoxy, furanylmethoxy, lower alkoxy-lower alkyl, lower alkanoyl, halogen, hydroxyl, cyano, carboxamido, acyloxy, or radicals of the formula —O—CH$_2$—X      III or —(CH$_2$)$_m$—X      IV, in which X in formulae III and IV in turn represents carbamoyl, alkylcarbamoyl, dialkylcarbamoyl, ureido, N'-alkylureido, N'-cycloalkylureido, N,N-dialkylureido, N',N'-dialkylureido or alkoxycarbonylamino and m in formula IV represents zero or an integer from 1 to 3,
(b) a fused-on polynuclear aromatic or hydroaromatic radical which may be mono- or polysubstituted by hydroxyl and/or may contain one or more oxo groupings,
$R_1$ is hydrogen or a straight-chain or branched $C_2$ to $C_5$-alkanoyl or aroyl radical,
$R_2$ is hydrogen and
$R_3$ is a branched $C_3$ to $C_6$-alkyl radical, a phenyl-lower alkyl or indolyl-lower alkyl radical which is straight-chain or branched and is unsubstituted or substituted by hydroxyl or alkoxy, or a radical of the formula —(CH$_2$)$_l$—Y      V, in which, in formula V, l represents the integer 1 to 2 and Y represents an N'-phenylureido, N'-pentamethyleneureido, N'-3''-oxapentamethyleneureido or unsubstituted or substituted phenylacetyl-amino radical; which comprises reacting an aryloxy-propanolamine of the formula

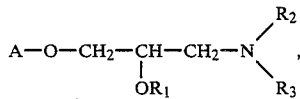

in which A, $R_1$, $R_2$ and $R_3$ are as defined above, with at least the stoichiometric amount of diphenylacetic acid in a solvent or solvent mixture which is inert towards the reaction partners, at temperatures from room temperature up to the boiling point of the solvent or the lowest-boiling solvent component, separating off the diphenylacetate of formula I which deposits at room temperature or, preferably, at low temperatures from the reaction mixture obtained in this reaction and, if appropriate, recrystallizing it from an organic solvent.

2. The process as claimed in claim 1, wherein a crude product such as is obtained in a synthesis route customary for the preparation of an aryloxy-propanolamine, after removal from the reaction mixture and without a further purification step, is employed as the aryloxy-propanolamine of the formula VI.

3. The process as claimed in claim 2, wherein a crude product such as is obtained by reaction of a 1-aryloxy-2,3-epoxy-propane of the formula

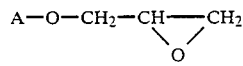

or a compound of the formula

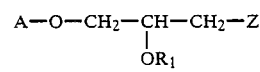

with the equivalent amount or a small, for example two-to three-fold, excess of an amine of the formula

in which, in the above formulae, A, $R_1$, $R_2$ and $R_3$ have the meaning given under formula I and Z represents a leaving group which can easily be split off, after removal from the reaction mixture, is employed as the aryloxy-propanolamine of the formula VI.

4. A process as claimed in claim 1, wherein the salt of formula I is a salt of N'-(3-acetyl-4-(3-((1,1-dimethylethyl)amino)-2-hydroxypropoxy)phenyl-N,N-diethylurea (celiprolol), 1,-((1-methylethyl)amino)-3-(1-naphthyloxy)-2-propanol (propranolol), 1-(2,3-dimethylphenoxy)-3-(1,1-dimethylethyl)amino-2-propanol (xibenol), 1-(2,5-dichlorophenoxy)-3-((1,1-dimethylethyl)amino)-2-propanol (cloranolol), 1-(2-chloro-5-methylphenoxy)-3-((1,1-dimethylethyl)amino)-2-propanol (bupranolol), 1-(4-(2-methoxyethyl)phenoxy)-3-((1-methylethyl)amino)-2-propanol (metoprolol), 4-(2-hydroxy-3-((1-methylethyl)amino)propoxy)-phenylacetamide (atenolol), N-(3-acetyl-4-(2-hydroxy-3-((1-methylethyl)amino)propoxy)phenyl)acetamide (diacetolol), 1-((1-methylethyl)amino)-3-(2-(2-propenyloxy)-phenoxy)-2-propanol (oxprenolol), 1-(3-methylphenoxy)-3-((2-(3,4-dimethoxyphenyl)ethyl)amino)-2-propanol (bevantolol), 2-(3-((1,1-dimethylethyl)amino)-2-hydroxypropoxy)benzonitrile (bunitrolol), N-(3-acetyl-4-(2-hydroxy-3-((1-methylethyl)amino)propoxy)phenyl)butyramide (acebutolol), N-(2-((3-(2-cyanophenoxy)-2-hydroxy-propyl)amino)ethyl)-2-(4-hydroxyphenyl)acetamide (epanolol), 1-(2,4-dichlorophenoxy)-3-(3,4-dimethoxy-β-phenylethylamino)-2-propanol, 4-(2-hydroxy-3-((1-methyl-3-phenylpropyl)-amino)-propoxy)phenyl-acetamide, N-(2-((3-(2-cyano-phenoxy)-2-hydroxy-propyl)amino)ethyl)-N'-phenylurea, 5-(3-((1,1-dimethylethyl)amino)-2-hydroxypropoxy)-3,4-dihydro-1-(2H)-naphthalinone (bunolol) or 2-(3-((1,1-dimethylpropyl)amino)-2-hydroxy-propoxy)benzonitrile (penirolol).

* * * * *